US009839783B2

(12) United States Patent
Schulhauser et al.

(10) Patent No.: US 9,839,783 B2
(45) Date of Patent: Dec. 12, 2017

(54) MAGNETIC FIELD DETECTORS, IMPLANTABLE MEDICAL DEVICES, AND RELATED METHODS THAT UTILIZE A SUSPENDED PROOF MASS AND MAGNETICALLY SENSITIVE MATERIAL

(71) Applicant: Medtronic, Inc., Minneapolis, MN (US)

(72) Inventors: Randal C. Schulhauser, Phoenix, AZ (US); Ralph B. Danzl, Tempe, AZ (US); Sharon Kohanna Murray, Gilbert, AZ (US); Michael F. Mattes, Arlington, TX (US)

(73) Assignee: Medtronic, Inc., Minneapolis, MN (US)

( * ) Notice: Subject to any disclaimer, the term of this patent is extended or adjusted under 35 U.S.C. 154(b) by 501 days.

(21) Appl. No.: 14/340,893

(22) Filed: Jul. 25, 2014

(65) Prior Publication Data

US 2016/0023002 A1 Jan. 28, 2016

(51) Int. Cl.
*A61N 1/37* (2006.01)
*A61N 1/39* (2006.01)
(Continued)

(52) U.S. Cl.
CPC ............ *A61N 1/3718* (2013.01); *A61B 5/055* (2013.01); *A61N 1/36128* (2013.01); *A61N 1/37* (2013.01);
(Continued)

(58) Field of Classification Search
None
See application file for complete search history.

(56) References Cited

U.S. PATENT DOCUMENTS 5,818,227 A * 10/1998 Payne .................. G01R 33/038
324/259
5,911,738 A 6/1999 Sikorski et al.
(Continued)

FOREIGN PATENT DOCUMENTS

WO 2014151370 A1 9/2014

OTHER PUBLICATIONS

Holmes, "Laser fabrication and assembly processes for MEMS", Proc. SPIE 4274, Laser Applications in Microelectronic and Optoelectronic Manufacturing VI, Jun. 29, 2001; pp. 297-306.*
(Continued)

*Primary Examiner* — Katherine Fernandez

(57) ABSTRACT

Magnetic field detectors include a proof mass suspended by deformable arms similar to a three dimensional accelerometer. The magnetic field detectors further include magnetically sensitive material present on the proof mass and/or deformable arms to cause movement of the proof mass and/or deformable arms when in the presence of a magnetic field. This movement is converted to an electrical signal and that electrical signal is compared to a reference to determine if a magnetic field of interest is present. The magnetic field detector may be included within an implantable medical device, and when the magnetic field detector indicates that a magnetic field of an MRI scanner is present, the implantable medical device may switch to an MRI mode of operation. The device may also switch back to a normal mode of operation once the MRI scanner is no longer detected such as after a predefined amount of time.

22 Claims, 6 Drawing Sheets

(51) Int. Cl.

| | | |
|---|---|---|
| *A61N 1/36* | (2006.01) | |
| *G01R 33/028* | (2006.01) | |
| *A61B 5/055* | (2006.01) | |
| *C23C 14/34* | (2006.01) | |
| *G01D 5/242* | (2006.01) | |
| *G01L 1/16* | (2006.01) | |
| *G01L 1/18* | (2006.01) | |
| *G01R 33/00* | (2006.01) | |

(52) U.S. Cl.
 CPC ............ *A61N 1/3925* (2013.01); *C23C 14/34* (2013.01); *G01D 5/242* (2013.01); *G01L 1/16* (2013.01); *G01L 1/18* (2013.01); *G01R 33/0052* (2013.01); *G01R 33/0283* (2013.01); *G01R 33/0286* (2013.01)

(56) References Cited

U.S. PATENT DOCUMENTS

| | | | |
|---|---|---|---|
| 6,038,475 | A | 3/2000 | Sikorski et al. |
| 6,233,811 | B1 | 5/2001 | Payne et al. |
| 6,580,947 | B1 | 6/2003 | Thompson |
| 6,937,906 | B2 | 8/2005 | Terry et al. |
| 6,963,779 | B1 | 11/2005 | Shankar |
| 7,219,549 | B2 | 5/2007 | Honkura et al. |
| 7,509,748 | B2 | 3/2009 | Xue et al. |
| 2004/0254455 | A1 | 12/2004 | Iddan |
| 2006/0271199 | A1 | 11/2006 | Johnson |
| 2008/0154342 | A1 | 6/2008 | Digby et al. |
| 2009/0243607 | A1 | 10/2009 | Mather et al. |
| 2010/0010338 | A1 | 1/2010 | van Dam et al. |
| 2010/0308830 | A1 | 12/2010 | Shankar et al. |
| 2011/0144478 | A1* | 6/2011 | Zabow ................... A61K 49/18 600/420 |
| 2012/0277817 | A1 | 11/2012 | Ellingson et al. |
| 2013/0268012 | A1 | 10/2013 | Sison |
| 2013/0289663 | A1* | 10/2013 | Newman .............. A61N 1/3718 607/62 |
| 2014/0184213 | A1* | 7/2014 | Thompson ......... G01R 33/0286 324/244.1 |
| 2014/0266170 | A1* | 9/2014 | Seeger ................... G01P 15/08 324/227 |

OTHER PUBLICATIONS

"A New Sping on Magnetic Sensors for Medical Devices", MDDI Magazine, Dec. 7, 2010.
MEMS 3-Axis Accelerometer, Fujitsu, www.fme.fujitsu.com.
MMS 2.8mm Implantable Magnetic Switch, www.electronics-manufacturers.com/products/mms, Dec. 7, 2010.
(PCT/US2015/039845) PCT Notification of Transmittal of the International Search Report and the Written Opinion of the International Searching Authority, dated Sep. 25, 2015, 11 pages.

* cited by examiner

MAGNETIC FIELD DETECTORS, IMPLANTABLE MEDICAL DEVICES, AND RELATED METHODS THAT UTILIZE A SUSPENDED PROOF MASS AND MAGNETICALLY SENSITIVE MATERIAL

TECHNICAL FIELD

Embodiments of this disclosure relate to magnetic field detectors as well as implantable medical devices and methods that may be used for purposes including detecting a magnetic resonance image (MRI) scanner. More particularly, embodiments relate to magnetic field detectors that utilize a suspended proof mass and magnetically sensitive material to detect the magnetic field.

BACKGROUND

Implantable medical device systems including those that provide electrical stimulation therapy for cardiac, neurological, or other purposes are susceptible to malfunction from certain external conditions. For instance, MRI scanners produce magnetic fields and high frequency electromagnetic energy that may cause various issues for an implantable medical device. In the case of an MRI, one issue is that the magnetic fields may cause false sensing of physiological signals that are used to control the electrical stimulation which may lead to improper stimulation.

In order to operate during the MRI scan, an implantable medical device may be programmed by an external device to enter an MRI mode of operation in order to continue to function appropriately. For example, the MRI mode may cease the sensing of physiological signals and provide electrical stimulation in a manner that does not rely on the sensing of such signals. While operating in the MRI mode may resolve the issue, the implantable medical device is manually programmed to enter into the mode which, in some instances, may be subject to human error. Furthermore, manually programming the implantable medical device just prior to the MRI procedure requires that the external device and specialized support personnel be available at the site of the MRI, resulting in a large service burden for the medical field.

SUMMARY

Embodiments disclosed herein address issues such as these and others by providing a magnetic field detector that may be included within an implantable medical device to allow the implantable medical device to detect the magnetic field of interest. The implantable medical device may then take an appropriate action including entering into a special mode of operation without intervention from an external programmer. The magnetic field detector employs a suspended proof mass similar to a three dimensional accelerometer as well as a magnetically sensitive material which provides a three-dimensional responsiveness to the magnetic fields of interest.

Embodiments provide a device for detecting a magnetic field that includes a proof mass, a chassis, and a plurality of deformable arms connected on one end to the proof mass and on the other end to the chassis to suspend the proof mass relative to the chassis. The deformable arms have an electrical characteristic that varies depending upon a degree of deformation. The device further includes a magnetically sensitive material located on at least one of the proof mass and the deformable arms, the magnetically sensitive material being responsive to the presence of a magnetic field by imposing a force on the deformable arms to cause deformation.

Embodiments provide an implantable medical device that includes a housing, stimulation circuitry within the housing that produces electrical stimulation signals, and a processor within the housing that controls the operation of the stimulation circuitry. The processor has multiple modes of operation, wherein the processor implements at least one of the modes when a magnetic field of interest is present. The implantable medical device also includes a magnetic field detector within the housing and in communication with the processor to provide a signal to the processor regarding a magnetic field. The magnetic field detector includes a proof mass, a chassis, and a plurality of deformable arms connected on one end to the proof mass and on the other end to the chassis to suspend the proof mass relative to the chassis. The deformable arms have an electrical characteristic that varies depending upon a degree of deformation. The magnetic field detector also includes a magnetically sensitive material located on at least one of the proof mass and the deformable arms, and the magnetically sensitive material is responsive to the presence of the magnetic field by imposing a force on the deformable arms to cause deformation.

Embodiments provide a method of detecting that an implantable medical device is in proximity to a magnetic resonance image (MRI) scanner. The method involves providing the implantable medical device with a magnetic field detector that includes a proof mass, a chassis, and a plurality of deformable arms connected on one end to the proof mass and on the other end to the chassis to suspend the proof mass relative to the chassis. The deformable arms have an electrical characteristic that varies depending upon a degree of deformation. The magnetic field detector further includes a magnetically sensitive material located on at least one of the proof mass and the deformable arms, the magnetically sensitive material being responsive to the presence of a magnetic field by imposing a force on the deformable arms to cause deformation. The method further involves upon placing the implantable medical device in proximity to the MRI scanner such that the magnetic field of the MRI scanner causes deformation of the deformable arms, generating an electrical signal that relates to the magnetic field of the MRI scanner. Additionally, the method involves detecting from the electrical signal that the implantable medical device is in proximity to the MRI scanner.

Embodiments provide a method of constructing a magnetic field detector that involves providing a structure that includes a proof mass, a chassis, and a plurality of deformable arms connected on one end to the proof mass and on the other end to the chassis to suspend the proof mass relative to the chassis. The deformable arms have an electrical characteristic that varies depending upon a degree of deformation. The method further involves applying a magnetically sensitive material onto at least one of the proof mass and the deformable arms, the magnetically sensitive material being responsive to the presence of a magnetic field by imposing a force on the deformable arms to cause deformation.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Embodiments disclosed herein provide magnetic field detectors that utilize a proof mass suspended by deformable arms like that of an accelerometer but also utilize a magnetically sensitive material that is applied to the proof mass and/or deformable arms. The magnetically sensitive material causes the proof mass and/or deformable arms to be responsive to magnetic fields. The magnetic fields result in deformation of the arms suspending the proof mass. Such deformation changes an electrical characteristic of the arms which is detected to signal the presence of the magnetic field. The inclusion of such a magnetic field detector within an implantable medical device allows the implantable medical device to detect the presence of magnetic fields of interest, such as the magnetic fields of an MRI scanner, which allows the implantable medical device to switch to an appropriate mode of operation.

Figure 1:
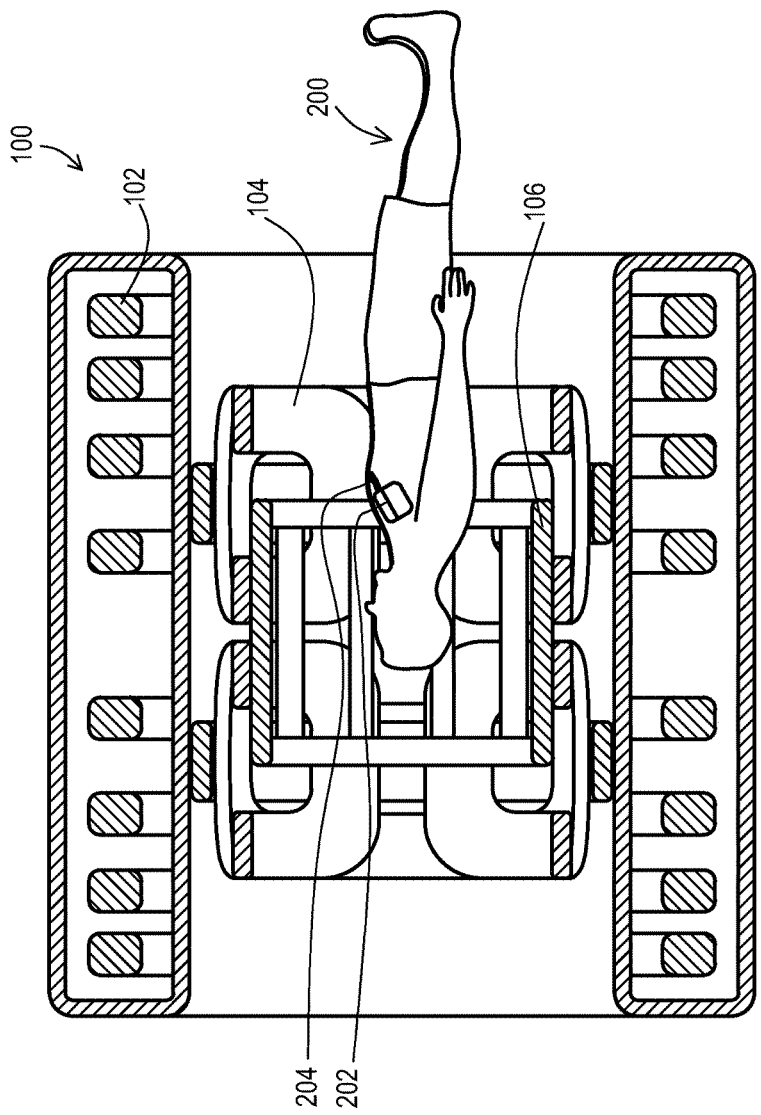
FIG. 1 shows an example of an MRI scanner while scanning a patient having an implantable medical system.

FIG. 1 shows a cross-sectional view of one example of an MRI scanner 100 with a patient 200 positioned within a bore of the MRI scanner 100 while undergoing an MRI scan. The MRI scanner 100 has several components that produce fields of various types. For instance, outer magnets 102 produce a static field that typically ranges from 1 to several Tesla in magnitude that passes through the patient 200. Inner magnets 104 produce gradient magnetic fields of orthogonal orientations that pass through the patient 200. A radiofrequency transceiving structure 106 produces radiofrequency fields within the patient 200 to create magnetic field oscillations within the patient 200. The static, gradient, and oscillating magnetic fields may all act upon a magnetic field detector introduced into the MRI scanner 100.

The patient 200 has an implantable medical system that includes an implantable medical device 202. In this example, the implantable medical system also includes an implantable medical lead 204 electrically and physically coupled to the implantable medical device 202. This implantable medical system may, for example, represent a pacemaker system, defibrillator system, cardioverter-defibrillator system, cardiac resynchronization system, cardiac loop recorder, or other implantable cardiac system that provides a combination of such therapies or other therapies or biophysiological monitoring. Alternatively, the implantable medical system may be a non-cardiac system, such as a neurostimulator that may deliver therapy (e.g., electrical signals or drugs) to a spinal cord, brain, pelvic floor or the like, to alleviate pain or treat symptoms of any of a number of neurological or other diseases, or other drug delivery system, such as a diabetes insulin pump or may provide biophysiological monitoring.

A magnetic field detector may be included within the implantable medical device 202 to allow the implantable medical device 202 to detect that the implantable medical device 202 is exposed to fluctuating and/or static magnetic fields of interest, and hence present within the MRI scanner 100 while the MRI scanner 100 is operational. In such a case, the implantable medical device 202 may then enter a mode of operation that is more appropriate for use during an MRI scan than a mode of operation being used when the implantable medical device 202 is not within the MRI scanner 100. This magnetic field detector may be responsive to the magnetic fields of the MRI scanner 100, and particularly, the oscillating magnetic field that very distinctively identifies the presence of the MRI scanner.

Figure 2:
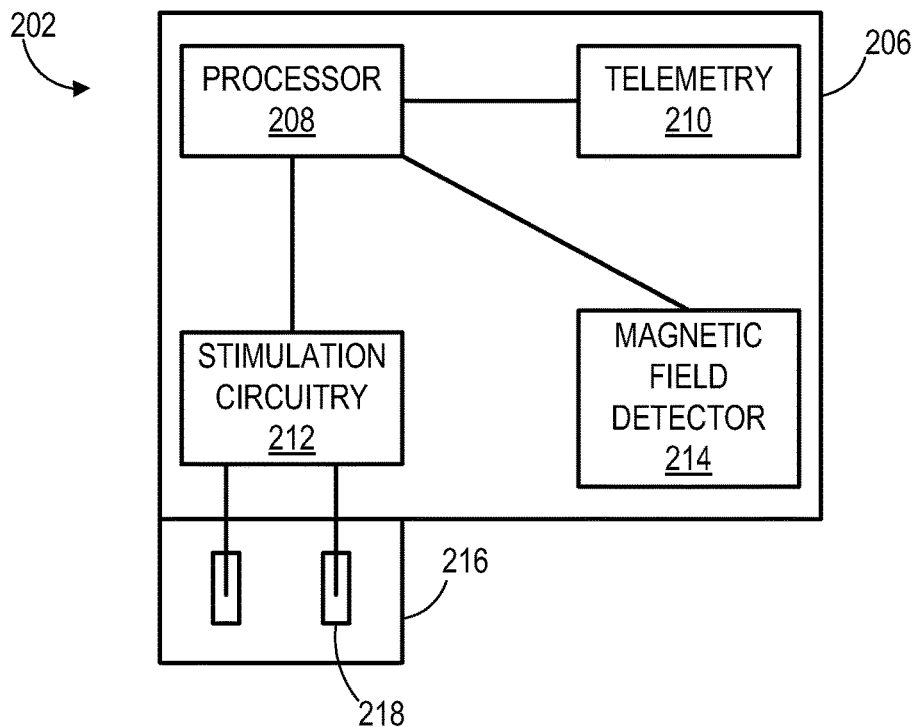
FIG. 2 shows an example of components of an implantable medical device having a magnetic field detector.

FIG. 2 shows an example of the implantable medical device 202 having various components including a magnetic field detector 214 enclosed within a housing 206. The implantable medical device 202 includes a processor 208 that acts as a controller to communicate with and control other components. The processor 208 may be of various forms such as a state machine, general purpose programmable processor, application specific processor, hard wired digital logic, and the like.

The implantable medical device 202 also includes medically related components within the housing 206 which in this example includes stimulation circuitry 212. The stimulation circuitry 212 provides stimulation signals to electrical connectors 218 within a header block 216. The implantable medical lead 204 of FIG. 1 is coupled to the header block 216 and is electrically coupled to the electrical connectors 218. The stimulation circuitry 212 may also include sensing functions to sense physiological signals that assist in determining the parameters of the stimulation signals being provided. Alternatively, implantable medical device 202 may include sensing circuitry that is separate from stimulation circuitry 212 and is also electrically coupled to processor 208 and electrical connectors 218. The processor 208 controls the operation of the stimulation circuitry 212 by activating and deactivating the stimulation and sensing functions and may also control the parameters of the stimulation signals.

The processor 208 is also in communication with telemetry circuit 210 within the housing 206 in this example. The telemetry circuit 210 allows the processor 208 to communicate with an external device to receive programming instructions and to send operational information, including sensed data, data regarding delivered therapies, device status data, and the like, that the patient or clinician may utilize when formulating programming instructions. The telemetry circuit 210 may provide near field telemetry, far field telemetry, or a combination.

The processor 208 additionally communicates with the magnetic field detector 214 that is present within the housing 206. The magnetic field detector 214 is responsive to magnetic fields to provide signals to the processor 208 that indicate the degree to which a magnetic field is present. The magnetic field detector 214 may have circuitry that provides a representation of the magnetic field to the processor 208, and the processor 208 may then analyze the representation of the magnetic field against a reference to determine if the magnetic field is that of an MRI scanner. As an alternative, the magnetic field detector 214 may itself have circuitry that analyzes the representation of the magnetic field against the reference to determine if the magnetic field is that of an MRI scanner and may signal to the processor 208 when the MRI scanner is present.

Figure 3:
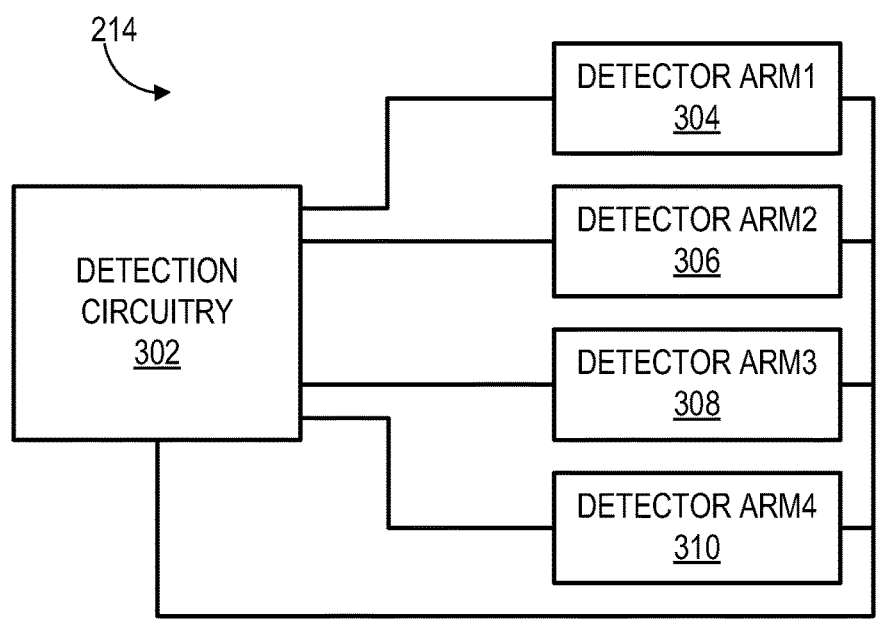
FIG. 3 shows a block diagram of one example of a magnetic field detector including detection circuitry.

FIG. 3 shows a diagram of an example of the magnetic field detector 214. The magnetic field detector 214 of this example includes detection circuitry 302 that is electrically connected to each deformable arm 304, 306, 308, and 310 being used to suspend a proof mass. While the example of FIG. 3 shows four deformable arms, it will be appreciated that other numbers of deformable arms are also applicable. The magnetic field detector 214 of FIG. 3 may be constructed as a three-dimensional accelerometer but may include a magnetically sensitive material so that detectable deformations of the arms 304, 306, 308, and 310 may be caused by the presence of magnetic fields. An example of this style of construction is described in more detail below with reference to FIG. 4. The sensitivity in three dimensions ensures that regardless of the orientation of the implantable medical device 202 within the patient 200, which can be unpredictable, there will be detectable deformations of the arms 304, 306, 308, and 310 to allow detection of the magnetic fields of interest.

The detection circuitry 302 of FIG. 3 may apply an electrical signal to each deformable arm 304, 306, 308, and 310 in a similar manner to a three dimensional accelerometer. For instance, the detection circuitry 302 may apply a direct current (DC) voltage or a voltage of a given frequency other than DC. The deformable arms 304, 306, 308, and 310 contain a material that has an electrical characteristic that varies with the degree of deformation of the arms.

For example, the deformable arms may be formed from or may otherwise contain a piezoresistive material that has a DC resistance that varies with the degree of deformation or a piezoelectric material that contributes a voltage depending upon the degree of deformation. The detection circuitry 302 may apply a DC voltage to the piezoelectric or piezoresistive material and then detect variations in the magnitude of current being drawn that are indicative of the magnetic field. The variations will have an oscillatory nature that matches the oscillation of the magnetic field from the MRI scanner 100. Thus, the detection circuitry 302, or processor 208, may compare the electrical current waveform to a reference waveform having the oscillations expected of the MRI scanner 100 in order to conclude that the MRI scanner 100 is present. As another example, the reference may be a frequency or range of frequencies and the detection circuitry 302 or processor 208 may analyze the electrical current waveform to determine the frequency of the oscillations and compare that frequency to the reference. Furthermore, the static field may produce a sustained deformation of the arms 304, 306, 308, and 310 that produces a signal that further signifies that the MRI scanner 100 is present.

As another example, the detection circuitry 302 may apply an alternating current with a frequency significantly different than the frequency of the oscillations of the magnetic field of the MRI scanner 100. Therefore, when the MRI scanner 100 is present, the oscillations can be detected within the alternating current being drawn from the voltage source by the arms 304, 306, 308, and 310. Another example involves the detection circuitry 302 applying either a direct or alternating current and monitoring for a change in the amplitude of the current being drawn. This change in amplitude of the signal results from the presence of the oscillating and/or static magnetic fields of the MRI scanner. For instance, the static field may cause a deformation of the arms 304, 306, 308, and 310 that is more substantial and sustained for a longer time than are produced by normal movements and positions of the patient.

Figure 4:
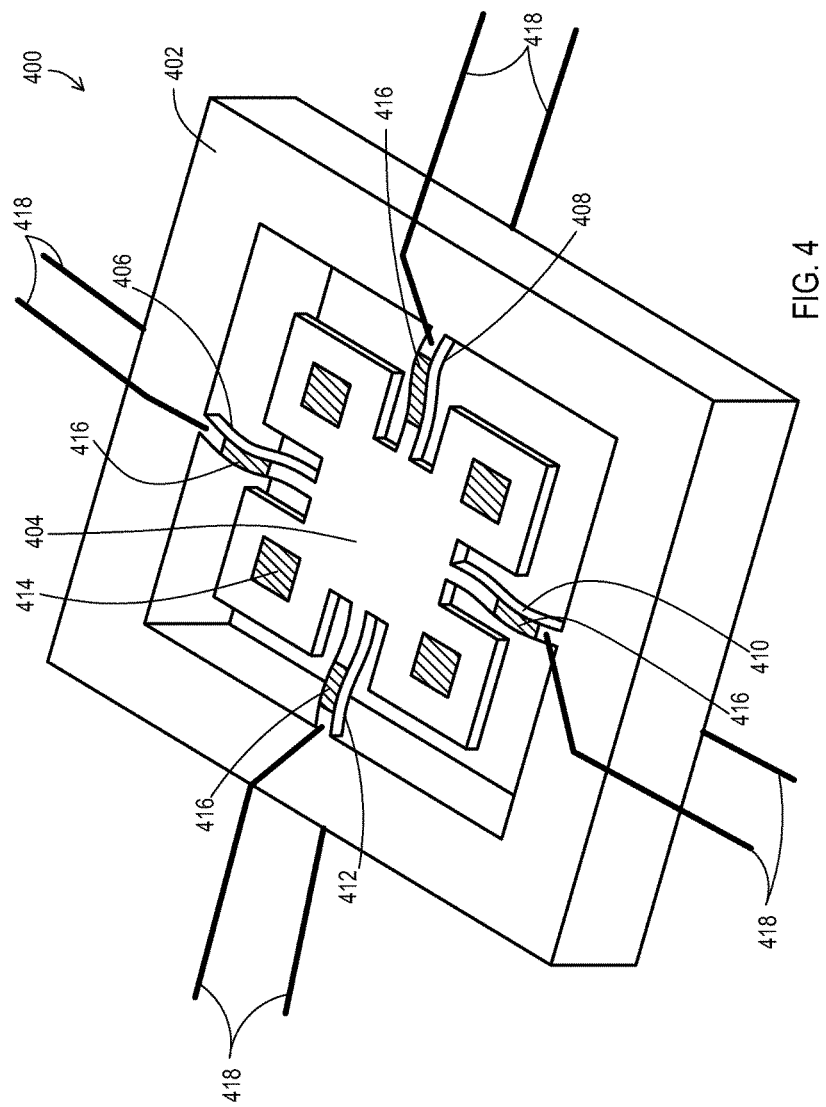
FIG. 4 shows an example of a magnetic field detector including a proof mass suspended by deformable arms.

FIG. 4 shows a structure 400 for one example of the magnetic field detector 214. This structure 400 is similar to a three dimensional accelerometer in that there is a chassis 402, a proof mass 404, and several deformable arms 406, 408, 410, and 412 that suspend the proof mass 404 from the chassis 402. However, in order to be responsive to magnetic fields, the structure 400 includes magnetically sensitive material in one or more locations so that the magnetic fields of the MRI scanner 100 interact with the magnetically sensitive material to impose a force on the proof mass 404 and/or deformable arms 406, 408, 410, and 412. In this example, magnetically sensitive material 414 is present on the proof mass 404 while magnetically sensitive material 416 is present on each of the deformable arms 406, 408, 410, and 412. It will be appreciated that the magnetically sensitive material may be present on only the arms, only the proof mass, or on both depending upon the degree of sensitivity that is desired and that more or less magnetically sensitive material may be included than is shown.

As discussed above in relation to FIG. 3, the deformable arms 406, 408, 410, and 412 of the example of FIG. 4 may include a material that has an electrical characteristic that varies when deformed. For example, the deformable arms 406, 408, 410, and 412 may be constructed of piezoelectric or piezoresistive material or may at least contain a layer of piezoelectric or piezoresistive material. Conductors 418 electrically connect the material of each arm having the electrical characteristic back to the detection circuitry. The arms may share a conductor on one side while there is an individual conductor for each arm on the other side where the current through each individual conductor may be monitored for oscillations indicative of the MRI scanner 100.

The chassis 402 and proof mass 404 may be constructed of various materials such as silicon. The arms 406, 408, 410, and 412 may also be constructed of silicon but with a layer of piezoelectric or piezoresistive materials deposited onto the arms either before or after the addition of the magnetically sensitive material. For instance, the piezoelectric or piezoresistive material may be sandwiched, secured to, or deposited on the seismic mass creating a double-cantilevered beam. Some examples of the piezoelectric materials include: quartz topaz, tourmaline, ceramics such as (BaTiO3)—barium titanate, lead titanate (PbTiO3), lead zirconate titanate (Pb[ZrxTi1-x]O3 $0 \leq x \leq 1$)—more commonly known as PZT, potassium niobate (KNbO3), lithium niobate (LiNbO3), lithium tantalate (LiTaO3), sodium tungstate (Na2WO3), and zinc oxide (ZnO). Some organic polymer examples include polyvinylidene fluoride, or polyvinylidene difluoride (PVDF). Some examples of piezoresistive materials include silicon with boron for a trace impurity for P-type material and arsenic as a trace impurity for N-type material.

The magnetically sensitive material 414, 416 that is added to either the arms and/or the proof mass may also be of various materials. Some examples of the magnetically sensitive material include iron oxide, ferric oxide, barium ferrite, and cobalt chrome. The mass of this magnetically sensitive material 414, 416 is small so that magnetic forces acting on the magnetically sensitive material 414, 416 produces adequate deformation of the arms 406, 408, 410, 412 but does not damage the arms 406, 408, 410, 412 or any other aspect of the structure 400 and does not present problematic forces on the device 102.

FIGS. 6-9 show logical operations related to constructing the magnetic field detector 214. At an operation 602 of FIG. 6, an accelerometer structure is provided by establishing the proof mass 404 suspended by deformable arms 406, 408, 410, and 412 from the chassis 402. This may be created by etching the details of the chassis 402, proof mass 404, and arms 406, 408, 410, and 412 from silicon. The piezoelectric or piezoresistive material may then be deposited onto the arms 406, 408, 410, and 412 and the electrical connections 418 are established thereafter.

Figure 7:
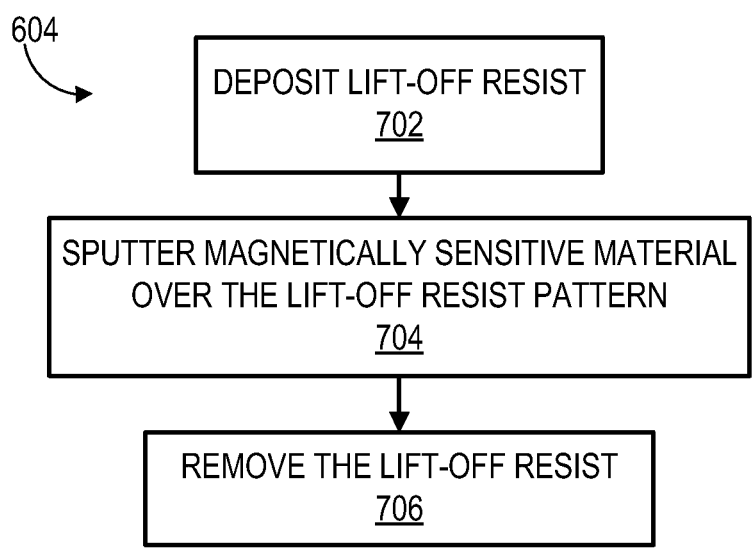
FIG. 7 shows a first example of a set of sub-operations to construct the magnetic field detector.
Figure 8:
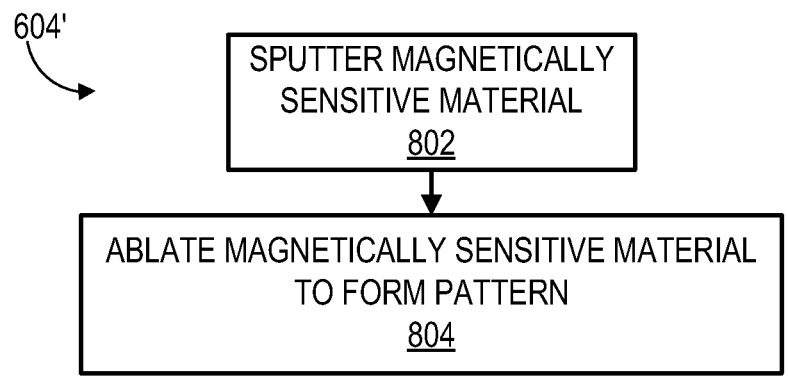
FIG. 8 shows a second example of a set of sub-operations to construct the magnetic field detector.
Figure 9:
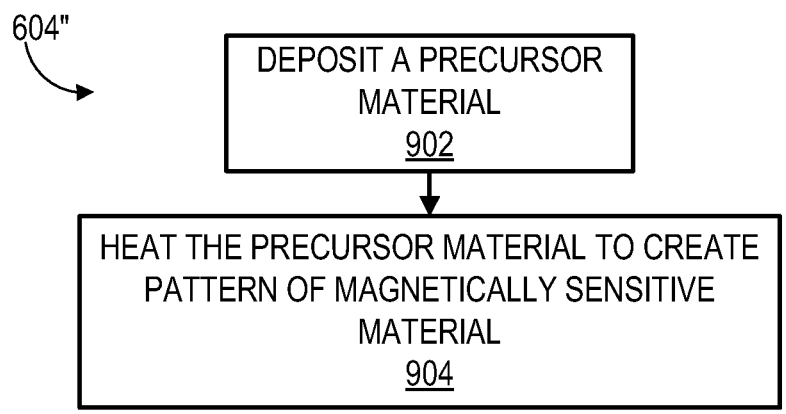
FIG. 9 shows a third example of a set of sub-operations to construct the magnetic field detector.

At an operation 604, the magnetically sensitive material is then added to the proof mass 404 and/or arms 406, 408, 410, and 412. There are various ways to add the magnetically sensitive material. Some examples are shown in FIGS. 7-9 and are discussed below. At an operation 606, the accelerometer structure having the magnetically sensitive material is then connected to the implantable medical device circuitry such as by connecting the conductors 418 to the detection circuitry 302 of FIG. 3.

One example 604 of the sub-operations is shown in FIG. 7. At a sub-operation 702, a lift-off resist material such as a photoresist liftoff, including those based on polymethylglutarimide, is deposited onto the proof mass and arms of the accelerometer structure and may be etched into a desired inverse pattern to cover those portions where magnetically sensitive material is not desired. At a sub-operation 704, the magnetically sensitive material is sputtered over the lift-off resist pattern and exposed areas to cover the lift-off resist material and the exposed portions of the underlying structure. The magnetically sensitive material adheres to the exposed portions. At a sub-operation 706, the lift-off resist material is removed which leaves behind the magnetically sensitive material in the areas that have been exposed while the areas that were covered by the lift-off resist material do not have magnetically sensitive material.

Another example of the sub-operations 604' is shown in FIG. 8. The magnetically sensitive material is sputtered onto the entire accelerometer structure including the arms and the proof mass at a sub-operation 802. Then, at a sub-operation 804 the magnetically sensitive material is laser ablated at areas where the magnetically sensitive material is not desired while leaving magnetically sensitive material in the other areas.

Another example of the operation 604" is shown in FIG. 9. A pre-cursor material is deposited onto the accelerometer structure at a sub-operation 902. The precursor material is then heated with a laser at the areas where the magnetically sensitive material is desired in order to convert the precursor material at the areas being heated to the magnetically sensitive material at a sub-operation 904. The pre-cursor material may be the magnetic material itself that may be deposited as a powder-like material that can be chemically altered with a laser applied to the areas where needed. A chemical bonding agent may be applied with the powder-like material to bond the material to the underlying structure. Other methods include depositing the magnetic material directly through a shadow mask in the desired areas.

Figure 5:
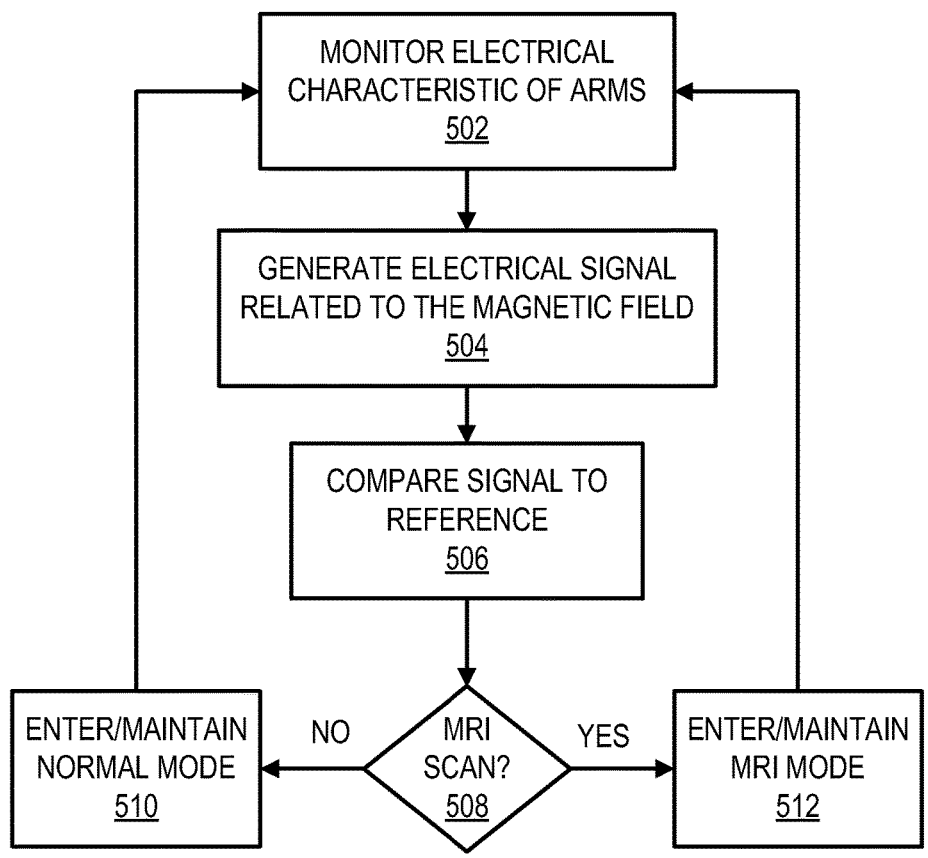
FIG. 5 shows an example of a set of operations that an implantable medical device may perform to change modes when in the presence of an MRI scan.
Figure 6:
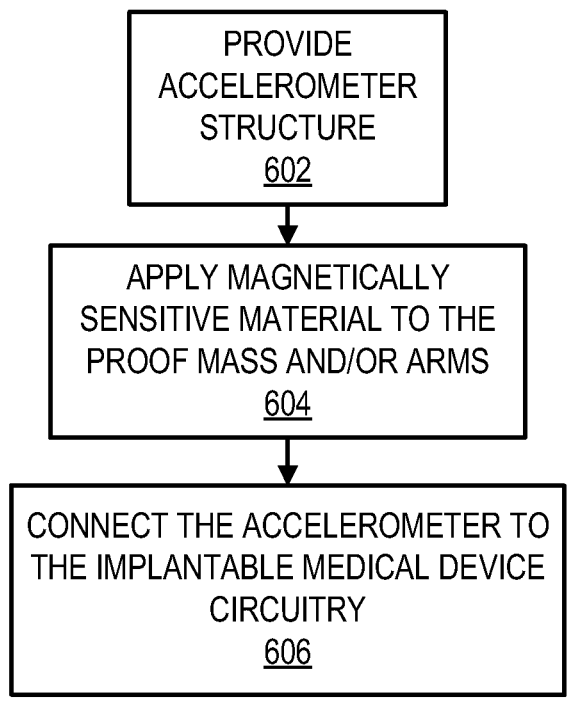
FIG. 6 shows an example of a set of operations to provide an implantable medical device with a magnetic field detector.

Once the magnetic field detector 214 has been constructed and installed within the implantable medical device 202, the operations of FIG. 5 may be conducted by the processor 208 in conjunction with the magnetic field detector 214. Initially, the magnetic field detector 214 may monitor the electrical characteristics of the deformable arms at an operation 502. The magnetic field detector 214 generates an electrical signal related to the magnetic field at an operation 504. For example, the magnetic field detector 214 may perform an analog to digital conversion to generate a digital representation of the current waveform being drawn by the deformable arms.

The representation of the current waveform may then be compared to a reference waveform or a reference value for frequency or other characteristic that corresponds to the signature of the magnetic field of interest at an operation 506. In this example, the reference represents the oscillatory nature of the MRI produced magnetic field. In one example, the processor 208 receives the digital representation and performs the comparison to the reference that is stored in memory. In that case, the processor 208 then detects at a query operation 508 whether the implantable medical device 202 is in close proximity to the MRI scanner 100. In another example, the magnetic field detector circuitry 302 may perform the comparison of the digital representation to the reference at the operation 506 and then may detect at the query operation 508 whether the implantable medical device 202 is in close proximity to the MRI scanner 100. In that case, the magnetic field detector circuitry 302 may then provide a signal to the processor 208 to indicate whether the MRI scanner 100 is present. The operations 506 and 508 may repeat at a desired interval.

Once the processor 208 has either determined that the MRI scanner 100 is not present or has received the signal from the magnetic field detector circuitry 302 that indicates that the MRI scanner 100 is not present, the processor 208 enters or maintains a normal mode at an operation 510. If the processor 208 had been implementing the normal mode, then that normal mode is maintained. If the processor 208 had been implementing the MRI mode, then the processor 208 switches the mode to the normal mode. In some examples, there may be a predefined period of time during which the MRI mode is maintained after it is detected that the operating MRI scanner 100 is not present before switching to the normal mode to ensure that the operating MRI scanner 100 is indeed no longer present.

Once the processor 208 has either determined that the MRI scanner 100 is present or has received the signal from the magnetic field detector circuitry 302 that indicates that the MRI scanner 100 is present, the processor 208 enters or maintains the MRI mode at an operation 512. If the processor 208 had been implementing the MRI mode, then that MRI mode is maintained. If the processor 208 had been implementing the normal mode, then the processor 208 switches the mode to the MRI mode and the iterations continue until again detecting that the MRI scanner 100 is no longer present so that the normal mode can again be activated. As discussed above, in some examples the device may switch back to the normal mode after the passing of a predefined period of time during which the MRI scanner 100 is not detected.

Accordingly, the implantable medical device 202 includes the magnetic field detector that utilizes the proof mass suspended by the deformable arms to determine the presence of magnetic fields including those of an MRI scanner 100. This allows the implantable medical device to adapt to the MRI environment by changing the mode of operation from a normal mode to an MRI mode without any instruction at that time from an external device.

While embodiments have been particularly shown and described, it will be understood by those skilled in the art that various other changes in the form and details may be made therein without departing from the spirit and scope of the invention.

What is claimed is:

1. A device for detecting a magnetic field, comprising:
a proof mass;
a chassis;
a plurality of deformable arms connected on one end to the proof mass and on the other end to the chassis to suspend the proof mass relative to the chassis, the deformable arms having an electrical characteristic that varies depending upon a degree of deformation;
a magnetically sensitive material located on at least one of the proof mass and the deformable arms, the magnetically sensitive material being responsive to the presence of a magnetic field by imposing a force on the deformable arms to cause deformation; and
circuitry electrically connected to the deformable arms, the circuitry being configured to produce a signal related to the magnetic field based on the electrical characteristic.

2. The device of claim 1, further comprising circuitry that determines whether the electrical characteristic varies in accordance with a reference.

3. The device of claim 2, wherein the reference is an oscillation corresponding to a magnetic field of a magnetic imaging resonance (MRI) scan.

4. The device of claim 1, wherein the magnetically sensitive material comprises at least one of ferric oxide, barium ferrite, and cobalt chrome.

5. The device of claim 1, wherein at least a portion of the arms comprise a piezoelectric or piezoresistive material to produce the variation in electrical characteristics for the degree of deformation.

6. An implantable medical device, comprising:
a housing;
stimulation circuitry within the housing that produces electrical stimulation signals;
a processor within the housing that controls the operation of the stimulation circuitry, the processor having multiple modes of operation, wherein the processor implements at least one of the modes when a magnetic field of interest is present; and
a magnetic field detector within the housing and in communication with the processor to provide a signal to the processor regarding a magnetic field, the magnetic field detector comprising:
a proof mass;
a chassis;
a plurality of deformable arms connected on one end to the proof mass and on the other end to the chassis to suspend the proof mass relative to the chassis, the deformable arms having an electrical characteristic that varies depending upon a degree of deformation;
a magnetically sensitive material located on at least one of the proof mass and the deformable arms, the magnetically sensitive material being responsive to the presence of the magnetic field by imposing a force on the deformable arms to cause deformation; and
detection circuitry electrically connected to the deformable arms and to the processor, the detection circuitry being configured to provide a signal related to the magnetic field to the processor.

7. The implantable medical device of claim 6, wherein the processor determines whether the electrical characteristic varies in accordance with a reference.

8. The implantable medical device of claim 7, wherein the reference is an oscillation corresponding to a magnetic field of a magnetic imaging resonance (MRI) scan.

9. The implantable medical device of claim 6 wherein the magnetically sensitive material comprises a ferrite.

10. The implantable medical device of claim 6, wherein at least a portion of the arms comprise a piezoelectric or piezoresistive material to produce the variation in electrical characteristics for the degree of deformation.

11. The implantable medical device of claim 6, further comprising an implantable medical lead that is electrically coupled to the stimulation circuitry.

12. A method of detecting that an implantable medical device is in proximity to a magnetic resonance image (MRI) scanner, comprising:
providing the implantable medical device with a magnetic field detector that comprises:
a proof mass;
a chassis;
a plurality of deformable arms connected on one end to the proof mass and on the other end to the chassis to suspend the proof mass relative to the chassis, the deformable arms having an electrical characteristic that varies depending upon a degree of deformation;
a magnetically sensitive material located on at least one of the proof mass and the deformable arms, the magnetically sensitive material being responsive to the presence of a magnetic field by imposing a force on the deformable arms to cause deformation; and
detection circuitry that is electrically connected to the deformable arms and configured to produce an electrical signal related to the magnetic field based on the electrical characteristic;
upon placing the implantable medical device in proximity to the MRI scanner such that the magnetic field of the MRI scanner causes deformation of the deformable arms, generating the electrical signal that relates to the magnetic field of the MRI scanner; and
detecting from the electrical signal that the implantable medical device is in proximity to the MRI scanner.

13. The method of claim 12, further comprising providing a signal related to the magnetic field.

14. The method of claim 13, further comprising comparing the signal to a reference.

15. The method of claim 14, wherein the reference is an oscillation corresponding to a magnetic field of the MRI scanner.

16. The method of claim 12 wherein the magnetically sensitive material comprises at least one of ferric oxide, barium ferrite, and cobalt chrome.

17. The method of claim 12, wherein at least a portion of the arms comprise a piezoelectric or piezoresistive material to produce the variation in electrical characteristics for the degree of deformation.

18. The method of claim 12, further comprising entering a mode of operation in response to detecting from the electrical signal that the implantable medical device is in proximity to the MRI scanner.

19. A method of constructing a magnetic field detector, comprising:
providing a structure that comprises:
a proof mass;
a chassis; and
a plurality of deformable arms connected on one end to the proof mass and on the other end to the chassis to suspend the proof mass relative to the chassis, the deformable arms having an electrical characteristic that varies depending upon a degree of deformation;
applying a magnetically sensitive material onto at least one of the proof mass and the deformable arms, the magnetically sensitive material being responsive to the presence of a magnetic field by imposing a force on the deformable arms to cause deformation; and electrically connecting the deformable arms to circuitry configured to produce a signal related to the magnetic field based on the electrical characteristic.

20. The method of claim 19, wherein applying the magnetically sensitive material comprises:

depositing a lift-off resist layer having a pattern that exposes areas of at least one of the proof mass and the arms;

sputtering the magnetically sensitive material over the pattern of the lift-off resist layer so that the magnetically sensitive material adheres to expose areas of at least one of the proof mass and the arms; and removing the lift-off resist layer.

21. The method of claim 19, wherein applying the magnetically sensitive material comprises:

sputtering the magnetically sensitive material onto at least one of the proof mass and the arms; and ablating the magnetically sensitive material with a laser to form a pattern on at least one of the proof mass and the arms.

22. The method of claim 19, wherein applying the magnetically sensitive material comprises:

depositing a precursor material onto at least one of the proof mass and the arms; and heating the precursor material with a laser to create a pattern of the magnetically sensitive material.

\* \* \* \* \*